(12) United States Patent
Lin et al.

(10) Patent No.: US 8,465,980 B2
(45) Date of Patent: Jun. 18, 2013

(54) URINE AND SERUM BIOMARKERS ASSOCIATED WITH DIABETIC NEPHROPATHY

(75) Inventors: Wei-Ya Lin, Tiachung County (TW); Mary Ya-Ping Yeh, Taipei (TW); Tzu-Ling Tseng, Taipei County (TW); Ping-Fu Cheng, Changhua County (TW); Tsai-Wei Hsu, Miaoli County (TW); Hung-Yi Li, Tainan County (TW); Yi-Ting Chen, Taoyuan County (TW); Yuh-Feng Ling, Taipei (TW); Jin-Shuen Chen, Taipei (TW); Yen-Peng Li, Taipei (TW)

(73) Assignee: Industrial Technology Research Institute, Hsin Chu (TW)

( * ) Notice: Subject to any disclaimer, the term of this patent is extended or adjusted under 35 U.S.C. 154(b) by 42 days.

(21) Appl. No.: 12/694,575

(22) Filed: Jan. 27, 2010

(65) Prior Publication Data

US 2010/0197033 A1  Aug. 5, 2010

Related U.S. Application Data

(60) Provisional application No. 61/147,778, filed on Jan. 28, 2009.

(51) Int. Cl.
 *G01N 33/53* (2006.01)
 *G01N 33/48* (2006.01)
(52) U.S. Cl.
 USPC ............................... 436/86; 436/87; 436/501
(58) Field of Classification Search
 USPC ..................................................... 436/86, 87
 See application file for complete search history.

(56) References Cited

FOREIGN PATENT DOCUMENTS

| WO | WO9915904 | 4/1999 |
|---|---|---|
| WO | WO-2007/051069 A2 * | 5/2007 |
| WO | WO2008092214 | 7/2008 |
| WO | WO2008116867 | 10/2008 |

OTHER PUBLICATIONS

Rao, P. V. et al. "Proteomic Identification of Urinary Biomarkers of Diabetic Nephropathy," Diabetes Care, 2007, 30, 629-637.*
Wang, T. J. et al. "Multiple Biomarkers for the Prediction of First Major Cardiovascular Events and Death," New England Journal of Medicine, 2006, 355, 2631-2639.*
Jain, S. et al. "Proteomic Analysis of Urinary Protein Markers for Accurate Prediction of Diabetic Kidney Disorder," Journal of the Association of Physicians of India, 2005, 53, 513-520.*
Yamaguchi, H. et al. "Progession of Diabetic Nephropathy Enhances the Plasma Osteopontin Level in Type 2 Diabetic Patients," Endocrine Journal 2004, 51, 499-504.*
Kaiser, T. "Capillary electrophoresis coupled to mass spectrometer for automated and robust polypeptide determination in body fluids for clinical use," Electrophoresis 2004, 25, 2044-2055.*
Jiang et al.; "Increased Urinary Excretion of Orosomucoid is a Risk Predictor of Diabetic Nephropathy"; Nephrology; 14:332-337 (2009).
Christiansen et al.; "Increased Urinary Orosomucoid Excretion is not Related to Impaired Renal Function in Patients with Type 2 Diabetes"; Sep. 26, 2008, abstract only.

* cited by examiner

*Primary Examiner* — Yelena G Gakh
*Assistant Examiner* — Michelle Adams
(74) *Attorney, Agent, or Firm* — Occhiuti Rohlicek & Tsao LLP

(57) ABSTRACT

Disclosed is use of urine and serum biomarkers in diagnosing diabetic nephropathy, staging diabetic nephropathy, monitoring diabetic nephropathy progress, and assessing efficacy of diabetic nephropathy treatments. These biomarkers include urine precursor alpha-2-HS-glycoprotein, urine alpha-1 antitrypsin, urine alpha-1 acid glycoprotein, urine osteopontin, serum osteopontin, their fragments, and combinations thereof.

22 Claims, 5 Drawing Sheets

A.

B.

C.

D.

| Table. Ratio of iTRAQ-derived Quantities | | | | |
|---|---|---|---|---|
| Protein [Homo sapiens] | DM:HC | HC:DM | DN116:DM | DN117:DM |
| DNO | 0.99 | 1.01 | 0.33 | 0.27 |
| DNA | 1.31 | 0.76 | 0.30 | 0.25 |

DNO

Custom-made,
peptide-based
Antibodies

DN2

DN5

DNO

DNA

```
SEQUENCE LISTING

<160> NUMBER OF SEQ ID NOS: 9

<210> SEQ ID NO 1
<211> LENGTH: 17
<212> TYPE: PRT
<213> ORGANISM: Artificial Sequence
<220> FEATURE:
<223> OTHER INFORMATION: Fragment of alpha-2-HS-glycoprotein

<400> SEQUENCE: 1

Val Val Ser Leu Gly Ser Pro Ser Gly Glu Val Ser His Pro Arg Lys
1               5                   10                  15

Thr

<210> SEQ ID NO 2
<211> LENGTH: 19
<212> TYPE: PRT
<213> ORGANISM: Artificial Sequence
<220> FEATURE:
<223> OTHER INFORMATION: Fragment of alpha-2-HS-glycoprotein

<400> SEQUENCE: 2

Met Gly Val Val Ser Leu Gly Ser Pro Ser Gly Glu Val Ser His Pro
1               5                   10                  15

Arg Lys Thr

<210> SEQ ID NO 3
<211> LENGTH: 18
<212> TYPE: PRT
<213> ORGANISM: Artificial Sequence
<220> FEATURE:
<223> OTHER INFORMATION: Fragment of alpha-1 antitrypsin

<400> SEQUENCE: 3

Lys Gly Lys Trp Glu Arg Pro Phe Glu Val Lys Asp Thr Glu Glu Glu
1               5                   10                  15

Asp Phe

<210> SEQ ID NO 4
<211> LENGTH: 21
<212> TYPE: PRT
<213> ORGANISM: Artificial Sequence
```

```
<220> FEATURE:
<223> OTHER INFORMATION: Fragment of alpha-1 antitrypsin

<400> SEQUENCE: 4

Met Ile Glu Gln Asn Thr Lys Ser Pro Leu Phe Met Gly Lys Val Val
1               5                   10                  15

Asn Pro Thr Gln Lys
            20

<210> SEQ ID NO 5
<211> LENGTH: 32
<212> TYPE: PRT
<213> ORGANISM: Artificial Sequence
<220> FEATURE:
<223> OTHER INFORMATION: Fragment of alpha-1 antitrypsin

<400> SEQUENCE: 5

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

<210> SEQ ID NO 6
<211> LENGTH: 34
<212> TYPE: PRT
<213> ORGANISM: Artificial Sequence
<220> FEATURE:
<223> OTHER INFORMATION: Fragment of alpha-1 antitrypsin

<400> SEQUENCE: 6

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala

<210> SEQ ID NO 7
<211> LENGTH: 32
<212> TYPE: PRT
<213> ORGANISM: Artificial Sequence
<220> FEATURE:
<223> OTHER INFORMATION: Fragment of alpha-1 acid glycoprotein

<400> SEQUENCE: 7

Gly Gln Glu His Phe Ala His Leu Leu Ile Leu Arg Asp Thr Lys Thr
1               5                   10                  15

Tyr Met Leu Ala Phe Asp Val Asn Asp Glu Lys Asn Trp Gly Leu Ser
            20                  25                  30

<210> SEQ ID NO 8
<211> LENGTH: 42
<212> TYPE: PRT
<213> ORGANISM: Artificial Sequence
<220> FEATURE:
<223> OTHER INFORMATION: Fragment of osteopontin

<400> SEQUENCE: 8

Tyr Pro Asp Ala Val Ala Thr Trp Leu Asn Pro Asp Pro Ser Gln Lys
1               5                   10                  15

Gln Asn Leu Leu Ala Pro Gln Asn Ala Val Ser Ser Glu Glu Thr Asn
            20                  25                  30

Asp Phe Lys Gln Glu Thr Leu Pro Ser Lys
            35                  40
```

```
<210> SEQ ID NO 9
<211> LENGTH: 29
<212> TYPE: PRT
<213> ORGANISM: Artificial Sequence
<220> FEATURE:
<223> OTHER INFORMATION: Fragment of osteopontin

<400> SEQUENCE: 9

Lys Tyr Pro Asp Ala Val Ala Thr Trp Leu Asn Pro Asp Pro Ser Gln
1               5                   10                  15

Lys Gln Asn Leu Leu Ala Pro Gln Thr Leu Pro Ser Lys
            20                  25
```

URINE AND SERUM BIOMARKERS ASSOCIATED WITH DIABETIC NEPHROPATHY

RELATED APPLICATION

This application claims priority to U.S. Provisional Application No. 61/147,778, filed on Jan. 28, 2009, the content of which is hereby incorporated by reference in its entirety.

BACKGROUND OF THE INVENTION

Diabetic nephropathy (DN) is a progressive kidney disease associated with longstanding diabetes mellitus. It causes abnormal fluid filtration and increased urinary albumin excretion, eventually leading to kidney failure.

DN displays no symptoms in its early course. As such, it is difficult to detect the incipiency of this disease. In fact, present diagnosis of DN depends on development of microalbuminuria, which occurs when kidney damage is already in place. The lack of an early diagnostic test prevents effective treatment of early stage DN.

It is of great importance to identify reliable biomarkers useful in diagnosing early stage DN.

SUMMARY OF THE INVENTION

The present invention is based on unexpected discoveries that a number of urine and serum proteins and their fragments, either alone or in combination, are differentially presented in DN patients as compared to DN-free subjects. These protein molecules are therefore useful markers for diagnosing early stage DN.

Accordingly, one aspect of this invention features a method of diagnosing DN in a subject. This method includes at least two steps: (i) determining in a subject suspected of having DN a level of a biomarker, and (ii) assessing whether the subject has DN based on the level of the biomarker. An increase in the level of the biomarker, as compared to that in a DN-free subject, indicates that the subject has DN.

The biomarker used in this diagnostic method is one of the four protein molecules listed below:

(i) a first urine protein molecule that is precursor alpha-2-HS-glycoprotein or a fragment thereof having at least ten amino acid residues, such as, mature alpha-2-HS-glycoprotein, VVSLGSPSGEVSHPRKT (SEQ ID NO:1), or MGVVSLGSPSGEVSHPRKT (SEQ ID NO:2);

(ii) a second urine protein molecule that is alpha-1 antitrypsin or a fragment thereof having at least ten amino acid residues, such as KGKWERPFEVKDTEEEDF (SEQ ID NO:3); MIEQNTKSPLFMGKVVNPTQK (SEQ ID NO:4), EDPQGDAAQKTDTSHHDQDHPTFNKITPNLAE (SEQ ID NO:5), or EDPQGDAAQKTDTSHHDQDHPTFNKITPNLAEFA (SEQ ID NO:6);

(iii) a third urine protein molecule that is a fragment of alpha-1 acid glycoprotein having at least ten amino acid residues, such as GQEHFAHLLILRDTKTYMLAFDVNDEKNWGLS (SEQ ID NO:7); and (iv) a serum protein molecule that is osteopontin or a fragment thereof having at least ten amino acid residues, such as YPDAVATWLNPDPSQKQNLLAPQNAVSSEETNDFKQETLPSK (SEQ ID NO:8) or KYPDAVATWLNPDPSQKQNLLAPQTLPSK (SEQ ID NO:9).

The diagnostic method described above can further include, after the assessing step, a step of correlating the biomarker level with the DN status (i.e., whether it is at early or late stage). When the biomarker is protein molecules (i) or (iv), an increase in its level relative to that in a DN-free subject is indicative of late stage DN. For a biomarker that is protein molecules (ii) or (iii), its level indicates the DN status when compared with pre-determined reference biomarker levels representing early and late stage DN.

In another aspect, the present invention features a method for assessing efficacy of a DN treatment in a subject (e.g., a human patient or a laboratory animal). This method includes determining in the subject pre-treatment and post-treatment levels of protein molecules (i), (ii), (iii), or (iv), and assessing efficacy of the treatment based on a change in the level of the biomarker after the treatment. If the post-treatment level of the biomarker remains the same or decreases as compared to the pre-treatment level of the biomarker, it indicates that the treatment is effective.

In yet another aspect, this invention features a method for determining a DN stage, including at least four steps: (i) obtaining a urine sample and optionally, a serum sample from a subject suspected of having diabetic nephropathy, (ii) determining in the sample(s) a level of one of the biomarkers listed in the preceding paragraph, (iii) calculating a disease score based on the level of the biomarker, and (iv) assessing the subject's diabetic nephropathy stage based on the disease score as compared to pre-determined cutoff values indicating different diabetic nephropathy stages. In this method, the calculating step can be performed by ridge regression analysis, factor analysis, discriminant function analysis, and logistic regression analysis.

The biomarker used in the just-described DN staging method is composed of at least two of the following five protein molecules: protein molecules (i)-(iv) listed above and protein molecule (v) that is urine osteopontin or its fragment described above. In one example, the biomarker is composed of all of the five protein molecules. In another example, it is composed of at least two of protein molecules (i)-(iii) and (v).

Alternatively, the biomarker is composed of at least two of the five protein molecules listed above and additionally, one or more clinical factors, e.g., age, gender, HbA1c, albumin-1creatinine ratio (ACR), and glomerular filtration rate (GFR).

In still another aspect, the present invention provides a method for monitoring DN progress based on the level of any of the above-mentioned biomarkers. This method includes obtaining two urine samples and optionally, two serum samples, within a time span of 2 weeks to 12 months (e.g., 2-24 weeks or 3-12 months) from a subject suspected of having DN, determining in the samples a level of one of the biomarkers, calculating disease scores based on the biomarker levels, and assessing DN progress in the subject based on the disease scores. The disease score for the later-obtained samples being greater than that for the earlier-obtained samples is indicative of DN exacerbation.

The biomarkers mentioned above can also be used to assess efficacy of a DN treatment. The treatment is effective if the post-treatment level of one of the biomarkers remains unchanged or decreases as compared to the pre-treatment level of the same biomarker.

The present invention further provides a kit for use in any of the methods described above. This kit includes two, three, or four antibodies with different antigen specificities. Each of these antibodies is capable of binding to one of (i) alpha-2-HS-glycoprotein, (ii) alpha-1 antitrypsin, (iii) alpha-1 acid glycoprotein, and (iv) osteopontin. In one example, this kit contains only antibodies specific to antigens to be detected (e.g., biomarkers associated with DN) for practice one of the methods disclosed herein. Namely, it consists essentially of such antibodies.

Also within the scope of this invention is an isolated antibody specifically binding one of the following peptide:

```
                                              (SEQ ID NO: 2)
MGVVSLGSPSGEVSHPRKT, (SEQ ID NO: 3)
KGKWERPFEVKDTEEEDF, (SEQ ID NO: 4)
MIEQNTKSPLFMGKVVNPTQK, (SEQ ID NO: 6)
EDPQGDAAQKTDTSHHDQDHPTFNKITPNLAEFA, (SEQ ID NO: 7)
GQEHFAHLLILRDTKTYMLADVNDEKNWGLS, (SEQ ID NO: 8)
YPDAVATWLNPDPSQKQ NLLAPQNAVSSEETNDFKQETLPSK,
and (SEQ ID NO: 9)
KYPDAVATWLNPDPSQKQNLLAPQTLPSK.
```

The terms "an isolated antibody" used herein refers to an antibody substantially free from naturally associated molecules. More specifically, a preparation containing the antibody is deemed as "an isolated antibody" when the naturally associated molecules in the preparation constitute at most 20% by dry weight. Purity can be measured by any appropriate method, e.g., column chromatography, polyacrylamide gel electrophoresis, and HPLC.

Any of the antibodies described above can be used in manufacturing a kit useful in practicing any of the methods of this invention.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWING

The drawing is first described.

DETAILED DESCRIPTION OF THE INVENTION

Figure 1:
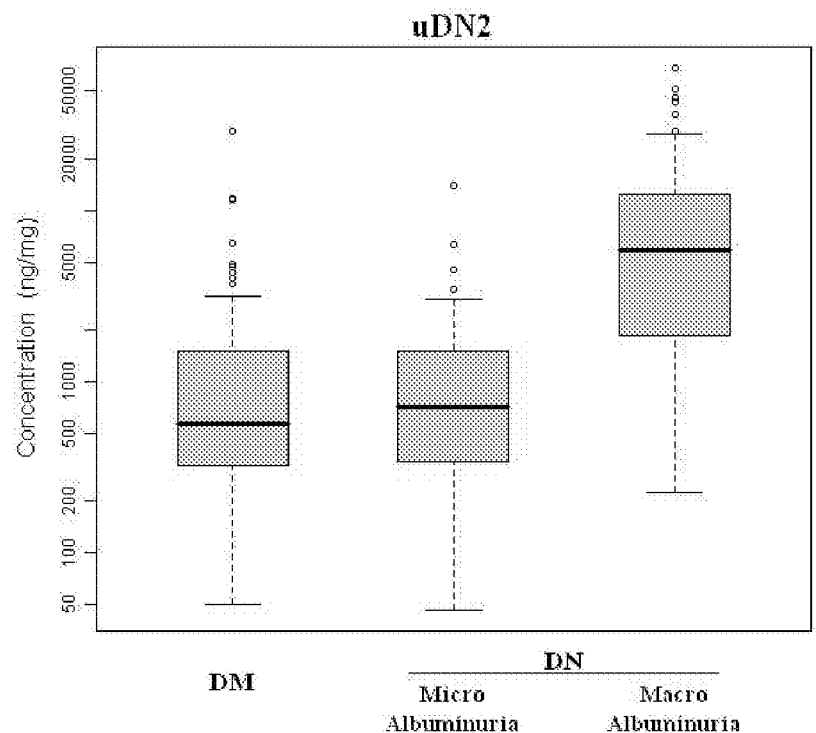
FIG. 1 is a diagram showing boxplots for urine alpha-2-HS-glycoprotein (uDN2; see panel A), urine alpha-1 antitrypsin (uDN5; see panel B), urine alpha-1 acid glycoprotein (uGR3; see panel C), and serum osteopontin (sDNO; see panel D) in various groups of DN patients. The upper and lower limits of the boxes mark the 25% and 75% values with the medians as the lines across the boxes. The upper whisker marks the largest value below the upper fence, which is the 75% value plus 1.5 interquartile range and the lower whisker marks the smallest value above the lower fence, which is the 25% value minus 1.5 interquartile range.
Figure 1:
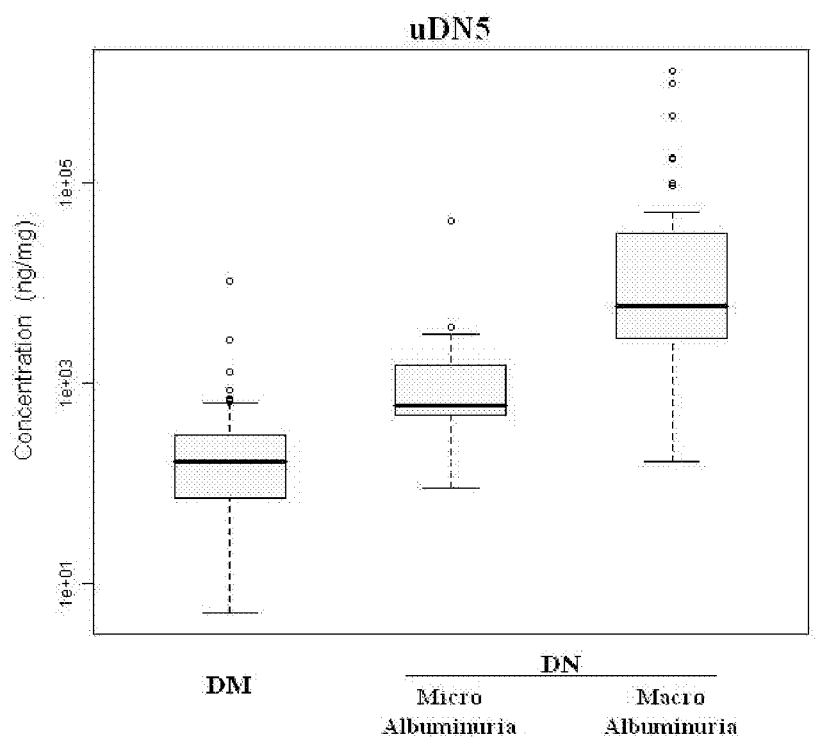
Figure 1:
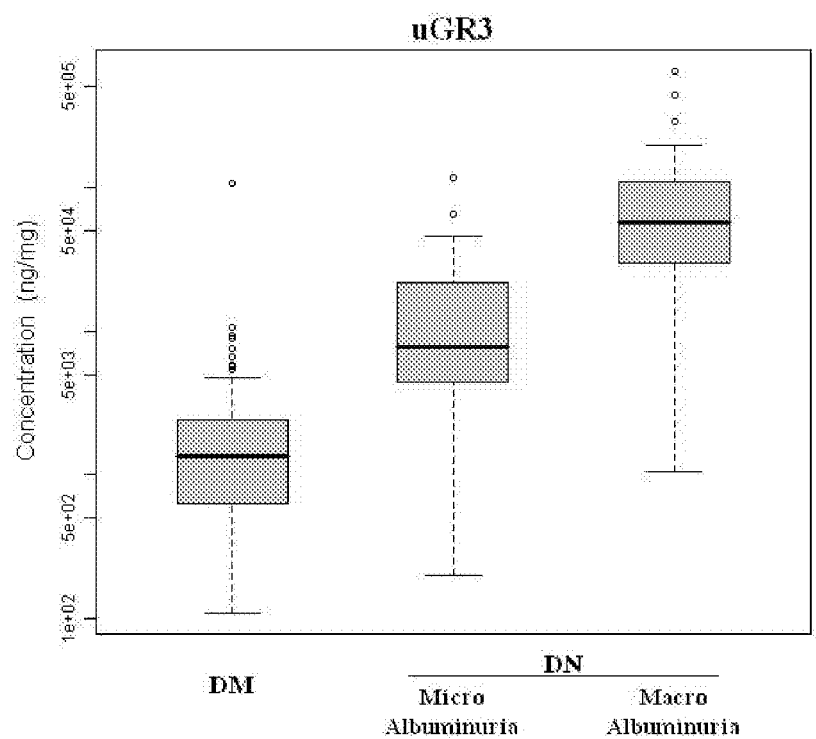
Figure 1:
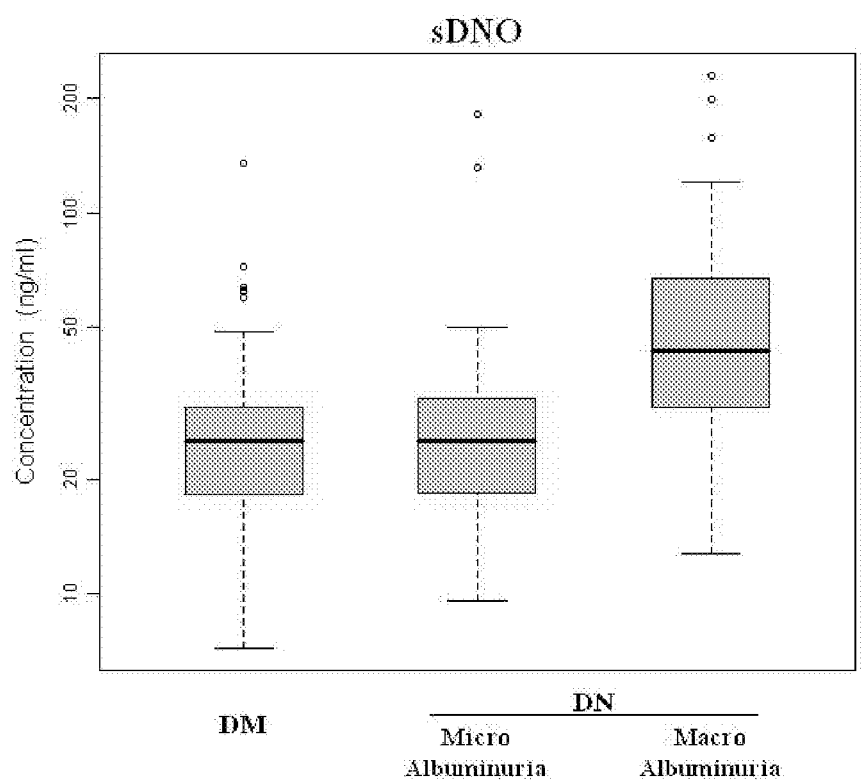

DN is a kidney disorder associated with diabetes. It has five progression phases:

Stage 1: characterized by diabetic mellitus with normal GFR and normal albuminuria (ACR<30 mg/g);

Stage 2: characterized by glomerular hyperfiltration (greater than 120 mL/minute/1.73 m$^2$) and renal enlargement accompanying with normal GFR and normal albuminuria (ACR<30 mg/g);

Stage 3: characterized by microalbuminuria;

Stage 4: characterized by overt albuminuria and a progressive decline in GFR; and Stage 5: characterized by a GFR of less than 15 mL/minute/1.73 m$^2$. Commonly, stages 1-3 are deemed as early stage and stages 4 and 5 are deemed as late stage.

We have identified a number of biomarkers associated with DN, especially DN in different stages. These biomarkers are composed of one or more of the following four proteins and their fragments, either in urine or in serum: (a) alpha-2-HS-glycoprotein (GenBank accession no. NP_001613; 10 Jan. 2010); (b) alpha-1-antitrypsin (GenBank accession no. AAB59495; 10 Jan. 2010); (c) alpha-1 acid glycoprotein (GenBank accession no. EAW87416; 10 Jan. 2010); and (d) Osteopontin, which includes two isoforms known as secreted phosphoprotein 1a (GenBank accession no. NP_001035147; 17 Jan. 2010) and secreted phosphoprotein 1b (GenBank accession no. NP_000573; 10 Jan. 2010,).

The fragments of these four proteins have a minimum length of ten amino acids and preferably, a maximum length of 190 to 410 amino acids. For example, fragments of proteins (a), (b), (c), and (d) can contain up to 357, 408, 191, and 290 amino acid residues, respectively.

We have also found that biomarkers composed of one or more of the above mentioned proteins/fragments, and one or more clinical factors (e.g., age, gender, HbA1c, ACR, and GFR) are also associated with DN in different stages.

Accordingly, one aspect of the present invention relates to a DN diagnostic method using any of the biomarkers described above. To practice this method, a urine sample and, when necessary, a serum sample, is collected from a subject suspected of having DN and the urine and serum levels of one or more of the four proteins listed above or their fragments can be determined via routine methods, e.g., mass spectrometry and immune analysis. If applicable, the clinical factors are determined by route methods.

When a biomarker contains a single protein molecule, its level in a subject can be compared with a reference point to determine whether that subject has DN. The reference point, representing the level of the same biomarker in a DN-free subject, can be determined based on the representative levels of the biomarker in groups of DN patients and DN-free subjects. For example, it can be the middle point between the mean levels of these two groups. A biomarker level higher than the reference point is indicative of DN.

When a biomarker contains at least two protein molecules and optionally, at least one clinical factor, the levels of the protein molecules and the value(s) of the clinical factor(s) can be subjected to a suitable analysis to generate a disease score (e.g., represented by a numeric number) that characterizes the level of the biomarkers. Examples of the analysis include, but are not limited to, discriminate function analysis, logistic regression analysis, ridge regression analysis, principal component analysis, factor analysis, and generalized linear model. The disease score is then compared with a reference point representing the level of the same biomarker in DN-free subjects. The reference point can be determined by conventional methods. For example, it can be a score obtained by analyzing the mean levels of the protein molecules and when necessary, the mean value(s) of the clinical factor(s) in DN-free subjects with the same analysis. The disease score being higher than the reference point is indicative of DN presence.

Another aspect of this invention relates to a method for determining a DN stage based on any of the biomarkers described above. To practice this method, a biomarker level of a DN patient, preferably represented by a disease score, is compared with a set of pre-determined cutoff values that distinguish different DN stages to determine the subject's DN stage. The cutoff values can be determined by analyzing the representative levels of the same biomarker in different-staged DN patients via the same analysis.

Described below is an exemplary procedure for determining the aforementioned cutoff values based on a biomarker associated with DN in different stages:

(1) assigning DN patients to different groups according to their disease conditions (e.g., DN stages and risk factors);

(2) determining in each patient group the levels/values of the protein molecules and clinical factors constituting the biomarker;

(4) subjecting the protein levels and clinical factor values to a suitable analysis to establish a model (e.g., formula) for calculating a disease score, and (6) determining a cutoff value for each disease stage based on a disease score (e.g., mean value) representing each patient group, as well as other relevant factors, such as sensitivity, specificity, positive predictive value (PPV) and negative predictive value (NPV).

Any of the models thus generated can be assessed for its diagnosis value by a receiver-operating characteristic (ROC) analysis to create a ROC curve. An optimal multivariable model provides a large Area under Curve (AUC) in the ROC analysis. See the models described in Examples 1-3 below.

In still another aspect, this invention relates to a method of monitoring nephropathy progress in a subject based on any of the biomarkers described above. More specifically, two urine samples and/or serum samples from a subject can be obtained within a suitable time span (e.g., 2 weeks to 12 months) and examined to determine the levels of one of the biomarkers. Disease scores are then determined as described above. If the disease score representing the biomarker level in the later obtained sample(s) is higher than that in the earlier-obtained sample(s), it indicates DN exacerbation in the subject.

The monitoring method can be applied to a human subject suffering from or at risk for DN. When the human subject is at risk for or in early stage DN, the level of the biomarker can be examined once every 6 to 12 months to monitor DN progress. When the human subject is already in late stage DN, it is preferred that the biomarker level be examined once every 3 to 6 months.

The monitoring method described above is also applicable to laboratory animals, following routine procedures, to study DN. The term "a laboratory animal" used herein refers to a vertebrate animal commonly used in animal testing, e.g., mouse, rat, rabbit, cat, dog, pig, and non-human primate. Preferably, a laboratory animal is examined to determine the biomarker level once every 2 to 24 weeks.

Any of the biomarkers can also be used to assess efficacy of a DN treatment in a subject in need (i.e., a human DN patient or a laboratory animal bearing DN). In this method, disease scores representing levels of one of the biomarkers described above are determined before, during, and after the treatment. If the disease scores remain the same or decline over the course of the treatment, it indicates that the treatment is effective.

Also disclosed herein is a kit useful in practicing any of the above-described methods. This kit contains two, three, or four antibodies with different antigen specificities. Each of these antibodies is capable of binding to one of (i) alpha-2-HS-glycoprotein, (ii) alpha-1 antitrypsin, (iii) alpha-1 acid glycoprotein, or (iv) osteopontin. The antibodies specific to proteins (i), (ii), (iii), and (iv) can bind to their fragments MGVVSLGSPSGEVSHPRKT (SEQ ID NO:2), KGKWERPFEVKDTEEEDF (SEQ ID NO:3), MIEQNTKSPLFMGKVVNPTQK (SEQ ID NO:4), EDPQGDAAQKTDTSHHDQDHPTFNKITPNLAEFA (SEQ ID NO:6), GQEHFAHLLILRDTKTYMLADVNDEKNWGLS (SEQ ID NO:7), YPDAVATWLNPDPSQKQNLLAPQNAVSSEETNDFKQETLPSK (SEQ ID NO:8), and KYPDAVATWLNPDPSQKQNLLAPQTLPSK (SEQ ID NO:9), i.e., specific to any antibody epitopes contained in these fragments. In one example, this kit contains only antibodies specific to antigens to be detected (e.g., protein molecules associated with DN) for practice one of the methods disclosed herein. Namely, the kit consists essentially of such antibodies.

The kit described above can include two different antibodies (i.e., a coating antibody and a detecting antibody) that bind to the same antigen. Typically, the detecting antibody is conjugated with a molecule which emits a detectable signal either on its own or via binding to another agent. The term "antibody" used herein refers to a whole immunoglobulin or a fragment thereof, such as Fab or F(ab')$_2$ that retains antigen-binding activity. It can be naturally occurring or genetically engineered (e.g., single-chain antibody, chimeric antibody, or humanized antibody).

The antibodies included in the kit of this invention can be obtained from commercial vendors. Alternatively, they can be prepared by conventional methods. See, for example, Harlow and Lane, (1988) Antibodies: A Laboratory Manual, Cold Spring Harbor Laboratory, New York. To produce antibodies against a particular biomarker as listed above, the marker, optionally coupled to a carrier protein (e.g., KLH), can be mixed with an adjuvant, and injected into a host animal. Antibodies produced in the animal can then be purified by affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*. Polyclonal antibodies, i.e., heterogeneous populations of antibody molecules, are present in the sera of the immunized animal.

Monoclonal antibodies, i.e., homogeneous populations of antibody molecules, can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

Moreover, antibody fragments can be generated by known techniques. For example, such fragments include, but are not limited to, $F(ab')_2$ fragments that can be produced by pepsin digestion of an antibody molecule, and Fab fragments that can be generated by reducing the disulfide bridges of $F(ab')_2$ fragments.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Diagnosing DN Based on Urine Alpha-2-HS-Glycoprotein, Urine Alpha-1 Antitrypsin, Urine Alpha-1 Acid Glycoprotein, or Serum Osteopontin Material and Methods
(i) Subjects 83 diabetic mellitus patients (designated "DM subjects"), and 82 DN patients (designated "DN subjects") were recruited at the Tri-General Military Hospital in Taipei, Taiwan, following the standards set forth by the American Diabetic Association and also described below:

DM: suffering from diabetic mellitus but free of DN (see the standards described below);

DN: suffering from diabetic mellitus and secreting urinary protein at a level greater than 1 g per day, having DN as proven by biopsy, or having uremia.

All of the subjects were assigned into a training group and a testing group at a ratio of 7:3.

(ii) Sample Collection and Processing

First-morning-void urinary samples and serum samples were collected from each of the subjects mentioned above. Peptides contained in the urine samples were examined by urinary matrix-assisted laser desorption/ionization time-of-flight mass spectrometry (MALDI-TOF-MS) and by isobaric tags for relative and absolute quantification (iTRAQ).

Protein molecules, including alpha-2-HS-glycoprotein (DN2), alpha-1 antitrypsin (DN5), osteopontin (DNO), and alpha-1 acid glycoprotein (GR3), were examined to determine their concentrations in both the urine and serum samples by ELISA. Briefly, urine samples were mixed with protease inhibitors and diluted at 1:100 with a dilution buffer and the serum samples were diluted at 1:10. The diluted samples were placed in ELISA plates in triplicates. The levels of DNO, DN2, DN5 and GR3 concentration were measured via the standard sandwich ELISA method.

A 5-parameter standard curve was used for concentration calculation. Only standards and samples with a coefficient of variation (CV) of less than 15% were included, and those not meeting criteria were repeated. The protein levels in the urine samples were normalized against the creatinine levels in the same urine samples, which were measured with the Quantichrome Creatinine Assay (BioAssay Systems, (Hayward)Calif., USA).

(iii) Statistical Analysis

The data indicating the urine and serum protein concentrations of each examined protein was statistically analyzed and performed as represented by auROC from 0.44-0.87 in their independent ability to distinguish DN subjects from DM subjects. For each subject, correlation between values was determined by Spearman or Pearson analysis depending on results of test for normality. Group mean or median comparisons were made with the Student T-test or the Nonparametric Mann-Whitney Test as appropriate. Statistical significance was obtained when p<0.05. Statistics were presented either as mean±standard error of mean (SEM) or as median with [25%, 75%].

Results
(i) Patient Characteristics

Tables 1 and 2 below show the characteristics of patients in the training group and testing group and those in DM, and DN groups:

TABLE 1

Characteristics of Patients in Training and Testing Groups

| | Training (n = 118) | Testing (n = 47) | P value |
|---|---|---|---|
| Age, mean (SD) | 59.94 (9.37) | 60.28 (9.48) | 0.8362 |
| Female, n (%) | 83 (70) | 27 (57) | 0.16 |
| MDRD_S_GFR, mean (SD) | 86.56 (33.11) | 83.05 (43.96) | 0.5785 |
| ACR (ug/mg), mean (SD) | 737.82 (1465.47) | 1084.18 (2030.98) | 0.2239 |
| Urine TP/Cr (mg/mg), mean (SD) | 1.01 (2.01) | 1 (1.78) | 0.9963 |
| Serum Creatinine (mg/dL), mean (SD) | 1.02 (0.87) | 1.34 (1.44) | 0.0903 |
| HbA1c (%), mean (SD) | 8.49 (1.5) | 8.29 (2.19) | 0.5356 |
| Markers (creatinine-adjusted), mean (SD) | | | |
| uDNO (ng/mg) | 1452.71 (1416.7) | 1488.77 (1222.2) | 0.8687 |
| sDNO (ng/ml) | 40.65 (34.52) | 38.35 (34.13) | 0.6926 |
| uDN2 (ng/mg) | 4225.77 (9279.63) | 5999.64 (10305.95) | 0.2983 |
| uDN5 (ng/mg) | 15951.12 (94956.78) | 45479.82 (199827.84) | 0.3228 |
| uGR3 (ng/mg) | 32823.47 (62290.96) | 42709.23 (103787.54) | 0.5333 |

MDRD_S_GFR: Modification of Diet in Renal Disease-Simplify-Glomerular Filtration Rate (ml/min/1.73 m$^2$)
TP/Cr: Total protein/Creatinine

TABLE 2

Characteristics of Patients in DM and DN Groups

| | Training (n = 118) | | | Testing (n = 47) | | |
|---|---|---|---|---|---|---|
| | DM (n = 61) | DN (n = 57) | P value | DM (n = 22) | DN (n = 25) | P value |
| Age, mean (SD) | 57.11 (8.05) | 62.96 (9.8) | 0.0006 | 59.09 (8.82) | 61.32 (10.09) | 0.4230 |
| Female, n (%) | 43 (70) | 40 (70) | 1.00 | 12 (55) | 15 (60) | 0.93 |
| MDRD_S_GFR, mean (SD) | 111.21 (15.75) | 60.18 (25.59) | <.0001 | 115.6 (33.66) | 54.41 (29.79) | <.0001 |
| ACR (ug/mg), mean (SD) | 11.35 (6.81) | 1515.26 (1815.72) | <.0001 | 9.63 (5.61) | 2029.78 (2432.31) | 0.0004 |
| Urine TP/Cr (mg/mg), mean (SD) | 0.17 (0.51) | 1.9 (2.56) | <.0001 | 0.17 (0.32) | 1.7 (2.18) | 0.0019 |
| Serum Creatinine (mg/dL), mean (SD) | 0.66 (0.12) | 1.42 (1.12) | <.0001 | 0.67 (0.15) | 1.92 (1.79) | 0.0019 |
| HbA1c (%), mean (SD) | 8.34 (1.48) | 8.7 (1.53) | 0.2311 | 8.37 (1.61) | 8.22 (2.66) | 0.8238 |
| Markers (creatinine-adjusted), mean (SD) | | | | | | |
| uDNO (ng/mg) | 1422.18 (1105.46) | 1366.77 (1347.92) | 0.8083 | 1769.54 (1260.15) | 1516.44 (1945.7) | 0.5953 |
| sDNO (ng/ml) | 29.03 (19.32) | 46.17 (37.32) | 0.0026 | 26.2 (11.53) | 64.52 (50.47) | 0.0010 |
| uDN2 (ng/mg) | 1968.47 (4218.58) | 8084.87 (13101.68) | 0.0013 | 968.79 (1144.47) | 7348.69 (10865.95) | 0.0074 |
| uDN5 (ng/mg) | 390.24 (1327.63) | 40036.86 (147186.58) | 0.0467 | 336.21 (568.08) | 71802.69 (264863.27) | 0.1899 |
| uGR3 (ng/mg) | 3576.06 (13562.8) | 67470.92 (105208.28) | <.0001 | 2447.77 (2742.38) | 71693.1 (82996.86) | 0.0003 |

Statistically significant differences in GFR, ACR, protein, and serum creatinine levels were observed in the DN subjects versus in the DM subjects. There was no difference in gender distribution among the groups.

(ii) Protein Molecules Associated with DN

Via urine proteomic analysis, the peptides listed in Table 3 below were found to be differentially presented in urine samples from the DM subjects and DN subjects:

TABLE 3

Differentially Presented Urine/Serum Peptides and Proteins in Which They are Located

| Peptide Sequences | Corresponding Proteins |
|---|---|
| VVSLGSPSGEVSHPRKT (SEQ ID NO: 1) | Alpha-2-HS glycoprotein (DN2) |
| MGVVSLGSPSGEVSHPRKT (SEQ ID NO: 2) | |
| KGKWERPFEVKDTEEEDF (SEQ ID NO: 3) | Alpha-1-antitrypsin (DN5) |
| MIEQNTKSPLFMGKVVNPTQK (SEQ ID NO: 4) | |
| EDPQGDAAQKTDTSHHDQDHPTFNKITPNLAE (SEQ ID NO: 5) | |
| EDPQGDAAQKTDTSHHDQDHPTFNKITPNLAEFA (SEQ ID NO: 6) | |

TABLE 3-continued

Differentially Presented Urine/Serum Peptides and Proteins in Which They are Located

| Peptide Sequences | Corresponding Proteins |
|---|---|
| YPDAVATWLNPDPSQKQ NLLAPQNAVSSEETNDFKQETLPSK (SEQ ID NO: 8) | Osteopontin (DNO) |
| GQEHFAHLLILRDTKTYMLAFDVNDEKNWGLS (SEQ ID NO: 7) | Alpha-1 acid glycoprotein (GR3) |

Via ELISA analysis, three urine protein molecules, i.e., uDN2, uGR3, and uDN5, and one serum protein molecule, i.e., sDNO, were found to be associated with DN. See FIG. 1, panels A-D and Table 2 above. More specifically, the levels of uDN2, uDN5, uGR3, and sDNO were found to be elevated in DN subjects as compared with DMs (free of DN), indicating that they are reliable markers for DN. Further, the levels of uDN5 and uGR3 in DN subjects exhibiting macroalbuminuria (ACR>300 mg/g) were higher than those in DN subjects exhibiting microalbuminuria (ACR 30 mg/g to 300 mg/g). Macroalbuminuria is an indicator of late stage DN and microalbuminuria indicates early stage DN.

EXAMPLE 2

Staging DN Based on a Combination of uDN2, uDN5, uGR3, uDNO, and sDNO

Two Protein Model

The combined levels of two of uDN2, uDN5, uGR3, uDNO, and sDNO in DM subjects, and DN subjects were subjected to discriminant function analysis, logistic regression analysis, and ridge regression analysis. The results from this study indicate that any combination of two of the five proteins or their fragments can be used as reliable markers for determining DN stages.

Shown below is an exemplary two-protein model, i.e., uDN5 and uGR3, including equations for calculating disease scores based on the combined levels of these two protein molecules. Also shown below are tables (i.e., Tables 4-9) listing cutoff values, sensitivities, specificities, positive predictive values (PPV) and negative predictive values (NPV), and area under the ROC curve (AUROC) for this two-protein model.

Discriminant Function Analysis:

$$\text{Disease Score} = 0.3303 \times \log_2[uDN5](\text{ng/mg}) + 0.2732 \times \log_2[uGR3](\text{ng/mg}) + 5$$

TABLE 4

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 11.227 | 11.691 | 11.227 | 11.691 |
| Sensitivity (%) | 93 | 93 | 96 | 100 |
| Specificity (%) | 90 | 90 | 77 | 83 |
| PPV (%) | 90 | 83 | 83 | 78 |
| NPV (%) | 93 | 96 | 94 | 100 |
| AUROC | 0.95 | 0.96 | 0.98 | 0.96 |

TABLE 5

Cutoff Values Representing DN Stages 1-5

| | Training set (n = 118) | | | | Testing set (n = 47) | | | |
|---|---|---|---|---|---|---|---|---|
| DN-Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 11.066 | 11.227 | 11.691 | 14.017 | 11.066 | 11.227 | 11.691 | 14.017 |
| Sensitivity (%) | 75 | 93 | 93 | 75 | 84 | 96 | 100 | 100 |
| Specificity (%) | 89 | 90 | 90 | 90 | 75 | 77 | 83 | 80 |
| PPV (%) | 92 | 90 | 83 | 21 | 87 | 83 | 78 | 18 |
| NPV (%) | 69 | 93 | 96 | 99 | 71 | 94 | 100 | 100 |
| AUROC | 0.86 | 0.95 | 0.96 | 0.95 | 0.9 | 0.98 | 0.96 | 0.91 |

Logistic Regression Analysis:

$$\text{Disease Score} = \exp(\text{Logit\_value})/(1+\exp(\text{Logit\_value})), \text{ in which}$$

$$\text{Logit\_value} = -12.5332 + 0.7197 \times \log_2[uDN5](\text{ng/mg}) + 0.4941 \times \log_2[uGR3](\text{ng/mg})$$

TABLE 6

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 0.445 | 0.676 | 0.445 | 0.676 |
| Sensitivity (%) | 93 | 93 | 100 | 100 |
| Specificity (%) | 90 | 90 | 82 | 83 |
| PPV (%) | 90 | 83 | 86 | 78 |
| NPV (%) | 93 | 96 | 100 | 100 |
| AUROC | 0.95 | 0.96 | 0.98 | 0.97 |

TABLE 7

Cutoff Values Representing DN Stages 1-5

| | Training set (n = 118) | | | | Testing set (n = 47) | | | |
|---|---|---|---|---|---|---|---|---|
| DN-Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 0.383 | 0.445 | 0.676 | 0.996 | 0.383 | 0.445 | 0.676 | 0.996 |
| Sensitivity (%) | 75 | 93 | 93 | 75 | 84 | 100 | 100 | 50 |
| Specificity (%) | 89 | 90 | 90 | 90 | 75 | 82 | 83 | 80 |
| PPV (%) | 92 | 90 | 83 | 21 | 87 | 86 | 78 | 10 |
| NPV (%) | 69 | 93 | 96 | 99 | 71 | 100 | 100 | 97 |
| AUROC | 0.86 | 0.95 | 0.96 | 0.95 | 0.9 | 0.98 | 0.97 | 0.88 |

Ridge Regression Analysis:

Disease Score=$-1.7697+0.1520\times\log_2[uDN5]$(ng/mg)$+0.2254\times\log_2[uGR3]$(ng/mg)

TABLE 8

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 2.254 | 2.606 | 2.254 | 2.606 |
| Sensitivity (%) | 93 | 93 | 100 | 94 |
| Specificity (%) | 90 | 90 | 77 | 79 |
| PPV (%) | 90 | 83 | 83 | 74 |
| NPV (%) | 93 | 96 | 100 | 96 |
| AUROC | 0.94 | 0.96 | 0.98 | 0.96 |

TABLE 9

Cutoff Values Representing DN Stages 1-5

| | Training set (n = 118) | | | | Testing set (n = 47) | | | |
|---|---|---|---|---|---|---|---|---|
| DN-Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 2.185 | 2.254 | 2.606 | 4.016 | 2.185 | 2.254 | 2.606 | 4.016 |
| Sensitivity (%) | 75 | 93 | 93 | 75 | 84 | 100 | 94 | 100 |
| Specificity (%) | 89 | 90 | 90 | 90 | 75 | 77 | 79 | 84 |
| PPV (%) | 92 | 90 | 83 | 21 | 87 | 83 | 74 | 22 |
| NPV (%) | 69 | 93 | 96 | 99 | 71 | 100 | 96 | 100 |
| AUROC | 0.86 | 0.94 | 0.96 | 0.95 | 0.89 | 0.98 | 0.96 | 0.91 |

Three Protein Model

The combined levels of three of uDN2, uDN5, uGR3, uDNO, and sDNO in DM subjects and DN subjects were subjected to discriminant function analysis, logistic regression analysis, factor analysis, and ridge regression analysis. The results indicate that any three-protein combination can be used as a reliable marker for DN staging.

Shown below is an exemplary three-protein model, i.e., uDN2, uDN5 and uGR3, including equations for calculating disease scores based on the combined levels of these three protein molecules. Also shown below are tables (i.e., Tables 10-17) listing cutoff values, sensitivities, specificities, PPV, NPV, and AUROC for this three-protein model.

Discriminant Function Analysis

Disease Score=$0.3340\times\log_2[uDN5]$(ng/mg)$-0.0142\times\log_2[uDN2]$(ng/mg)$+0.2784\times\log_2[uGR3]$(ng/mg)$+5$

TABLE 10

Cutoff Values Representing DN Early and Late Stages Indicated by Urine Albumin Levels

|  | Training set (n = 118) | | Testing set (n = 47) | |
|---|---|---|---|---|
|  | DM vs. DN | DM, Micro albuminuria vs. Macro albuminuria | DM vs. DN | DM, Micro albuminuria vs. Macro albuminuria |
| Cut-off | 11.190 | 11.663 | 11.190 | 11.663 |
| Sensitivity (%) | 93 | 93 | 96 | 100 |
| Specificity (%) | 90 | 90 | 77 | 83 |
| PPV (%) | 90 | 83 | 83 | 78 |
| NPV (%) | 93 | 96 | 94 | 100 |
| AUROC | 0.95 | 0.96 | 0.98 | 0.96 |

TABLE 11

Cutoff Values Representing DN Stages 1-5

|  | Training set (n = 118) | | | | Testing set (n = 47) | | | |
|---|---|---|---|---|---|---|---|---|
| DN Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 11.064 | 11.190 | 11.663 | 13.986 | 11.064 | 11.190 | 11.663 | 13.986 |
| Sensitivity (%) | 75 | 93 | 93 | 75 | 84 | 96 | 100 | 100 |
| Specificity (%) | 89 | 90 | 90 | 90 | 75 | 77 | 83 | 82 |
| PPV (%) | 92 | 90 | 83 | 21 | 87 | 83 | 78 | 20 |
| NPV (%) | 69 | 93 | 96 | 99 | 71 | 94 | 100 | 100 |
| AUROC | 0.87 | 0.95 | 0.96 | 0.95 | 0.9 | 0.98 | 0.96 | 0.91 |

Factor Analysis

Disease Score = $0.9190 \times \log_2[uDN5](ng/mg) + 0.6997 \times \log_2[uDN2](ng/mg) + 0.9003 \times \log_2[uGR3](ng/mg)$

TABLE 12

Cutoff Values Representing DN Early and Late Stages Indicated by Urine Albumin Levels

|  | Training set (n = 118) | | Testing set (n = 47) | |
|---|---|---|---|---|
|  | DM vs. DN | DM, Micro albuminuria vs. Macro albuminuria | DM vs. DN | DM, Micro albuminuria vs. Macro albuminuria |
| Cut-off | 26.356 | 28.057 | 26.356 | 28.057 |
| Sensitivity (%) | 84 | 93 | 88 | 100 |
| Specificity (%) | 90 | 90 | 91 | 86 |
| PPV (%) | 89 | 83 | 92 | 82 |
| NPV (%) | 86 | 96 | 87 | 100 |
| AUROC | 0.93 | 0.95 | 0.99 | 0.97 |

TABLE 13

Cutoff Values Representing DN Stages 1-5

|  | Training set (n = 118) | | | | Testing set (n = 47) | | | |
|---|---|---|---|---|---|---|---|---|
| DN Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 25.669 | 26.356 | 28.057 | 36.464 | 25.669 | 26.356 | 28.057 | 36.464 |
| Sensitivity (%) | 68 | 84 | 93 | 75 | 84 | 88 | 100 | 50 |
| Specificity (%) | 89 | 90 | 90 | 90 | 88 | 91 | 86 | 84 |
| PPV (%) | 91 | 89 | 83 | 21 | 93 | 92 | 82 | 12 |
| NPV (%) | 63 | 86 | 96 | 99 | 74 | 87 | 100 | 97 |
| AUROC | 0.83 | 0.93 | 0.95 | 0.95 | 0.91 | 0.99 | 0.97 | 0.86 |

Logistic Regression Analysis:

Disease Score=exp(Logit_value)/(1+exp(Logit_value)), in which

Logit_value=−11.2820+0.8810×log$_2$[uDN5](ng/mg)−0.3478×log$_2$[uDN2](ng/mg)+0.5576×log$_2$[uGR3](ng/mg)

TABLE 14

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 0.462 | 0.798 | 0.462 | 0.798 |
| Sensitivity (%) | 91 | 88 | 96 | 94 |
| Specificity (%) | 90 | 90 | 82 | 83 |
| PPV (%) | 90 | 82 | 86 | 77 |
| NPV (%) | 92 | 93 | 95 | 96 |
| AUROC | 0.95 | 0.96 | 0.97 | 0.95 |

TABLE 15

Cutoff Values Representing DN Stages 1-5

| | Training set (n = 118) | | | | Testing set (n = 47) | | | |
|---|---|---|---|---|---|---|---|---|
| DN Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 0.361 | 0.462 | 0.798 | 0.997 | 0.361 | 0.462 | 0.798 | 0.997 |
| Sensitivity (%) | 75 | 91 | 88 | 75 | 90 | 96 | 94 | 100 |
| Specificity (%) | 89 | 90 | 90 | 90 | 75 | 82 | 83 | 82 |
| PPV (%) | 92 | 90 | 82 | 21 | 88 | 86 | 77 | 20 |
| NPV (%) | 69 | 92 | 93 | 99 | 80 | 95 | 96 | 100 |
| AUROC | 0.88 | 0.95 | 0.96 | 0.95 | 0.89 | 0.97 | 0.95 | 0.93 |

Ridge Regression Analysis:

Disease Score=−1.2900+0.1800×log$_2$[uDN5](ng/mg)−0.1013×log$_2$[uDN2](ng/mg)+0.2505×log$_2$[uGR3](ng/mg)

TABLE 16

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 2.122 | 2.831 | 2.122 | 2.831 |
| Sensitivity (%) | 95 | 85 | 100 | 94 |
| Specificity (%) | 90 | 90 | 68 | 86 |
| PPV (%) | 90 | 81 | 78 | 81 |
| NPV (%) | 95 | 92 | 100 | 96 |
| AUROC | 0.95 | 0.95 | 0.97 | 0.95 |

TABLE 17

Cutoff Values Representing DN Stages 1-5

| DN Stage | Training set (n = 118) | | | | Testing set (n = 47) | | | |
|---|---|---|---|---|---|---|---|---|
| | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 2.083 | 2.122 | 2.831 | 3.943 | 2.083 | 2.122 | 2.831 | 3.943 |
| Sensitivity (%) | 78 | 95 | 85 | 75 | 87 | 100 | 94 | 100 |
| Specificity (%) | 89 | 90 | 90 | 90 | 69 | 68 | 86 | 82 |
| PPV (%) | 92 | 90 | 81 | 21 | 84 | 78 | 81 | 20 |
| NPV (%) | 71 | 95 | 92 | 99 | 73 | 100 | 96 | 100 |
| AUROC | 0.88 | 0.95 | 0.95 | 0.95 | 0.89 | 0.97 | 0.95 | 0.93 |

Four-protein model

The combined levels of four of uDN2, uDN5, uGR3, uDNO, and sDNO in DM subjects and DN subjects were subjected to discriminant function analysis, logistic regression analysis, factor analysis, and ridge regression analysis. The results indicate that any combination of four of the five proteins or their fragments can be used as a reliable marker for determining DN stages.

Shown below is an exemplary four-protein model, i.e., uDN2, uDN5, uGR3, and sDNO, including equations for calculating disease scores based on the combined levels of these four protein molecules. Also shown below are tables (i.e., Tables 18-25) listing cutoff values, sensitivities, specificities, PPVs, NPVs, and AUROC for this four-protein model.

Discriminant Function Analysis:

Disease Score=$0.2972 \times \log_2[uDN5](ng/mg) + 0.0159 \times \log_2[uDN2](ng/mg) + 0.2014 \times \log_2[uGR3](ng/mg) + 0.5688 \times \log_2[sDNO](ng/ml) + 5$

TABLE 18

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 12.945 | 13.520 | 12.945 | 13.520 |
| Sensitivity (%) | 88 | 95 | 96 | 100 |
| Specificity (%) | 90 | 90 | 82 | 86 |
| PPV (%) | 89 | 83 | 86 | 82 |
| NPV (%) | 89 | 97 | 95 | 100 |
| AUROC | 0.94 | 0.96 | 0.97 | 0.97 |

TABLE 19

Cutoff Values Representing DN Stages 1-5

| DN-Stages | Training set (n = 118) | | | | Testing set (n = 47) | | | |
|---|---|---|---|---|---|---|---|---|
| | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 12.887 | 12.945 | 13.520 | 15.560 | 12.887 | 12.945 | 13.520 | 15.560 |
| Sensitivity (%) | 73 | 88 | 95 | 100 | 81 | 96 | 100 | 100 |
| Specificity (%) | 89 | 90 | 90 | 90 | 81 | 82 | 86 | 82 |
| PPV (%) | 91 | 89 | 83 | 27 | 89 | 86 | 82 | 20 |
| NPV (%) | 67 | 89 | 97 | 100 | 68 | 95 | 100 | 100 |
| AUROC | 0.87 | 0.94 | 0.96 | 0.97 | 0.93 | 0.97 | 0.97 | 0.89 |

Factor Analysis:

Disease Score=$0.9132 \times \log_2[uDN5](ng/mg) + 0.6950 \times \log_2[uDN2](ng/mg) + 0.9080 \times \log_2[uGR3](ng/mg) + 0.4549 \times \log_2[sDNO](ng/ml)$

TABLE 20

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 28.459 | 30.095 | 28.459 | 30.095 |
| Sensitivity (%) | 82 | 93 | 92 | 100 |

TABLE 20-continued

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Specificity (%) | 90 | 90 | 91 | 83 |
| PPV (%) | 89 | 83 | 92 | 78 |
| NPV (%) | 85 | 96 | 91 | 100 |
| AUROC | 0.93 | 0.96 | 0.99 | 0.98 |

TABLE 21

Cutoff Values Representing DN Stages 1-5

| | Training set (n = 118) | | | | Testing set (n = 47) | | | |
|---|---|---|---|---|---|---|---|---|
| DN-Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 28.347 | 28.459 | 30.095 | 38.624 | 28.347 | 28.459 | 30.095 | 38.624 |
| Sensitivity (%) | 67 | 82 | 93 | 75 | 81 | 92 | 100 | 50 |
| Specificity (%) | 89 | 90 | 90 | 90 | 94 | 91 | 83 | 84 |
| PPV (%) | 91 | 89 | 83 | 21 | 96 | 92 | 78 | 12 |
| NPV (%) | 62 | 85 | 96 | 99 | 71 | 91 | 100 | 97 |
| AUROC | 0.84 | 0.93 | 0.96 | 0.95 | 0.92 | 0.99 | 0.98 | 0.86 |

Logistic Regression Analysis:

Disease Score = exp(Logit_value)/(1+exp(Logit_value)), in which $$\text{Logit\_value} = -13.7529 + 0.9460 \times \log_2[uDN5](\text{ng/mg}) - 0.3110 \times \log_2[uDN2](\text{ng/mg}) + 0.4957 \times \log_2[uGR3](\text{ng/mg}) + 0.4787 \times \log_2[sDNO](\text{ng/ml})$$

TABLE 22

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 0.423 | 0.804 | 0.423 | 0.804 |
| Sensitivity (%) | 91 | 88 | 96 | 100 |
| Specificity (%) | 90 | 90 | 77 | 86 |
| PPV (%) | 90 | 82 | 83 | 82 |
| NPV (%) | 92 | 93 | 94 | 100 |
| AUROC | 0.96 | 0.96 | 0.97 | 0.96 |

TABLE 23

Cutoff Values Representing DN States 1-5

| | Training set (n = 118) | | | | Testing set (n = 47) | | | |
|---|---|---|---|---|---|---|---|---|
| DN-Stages | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 0.341 | 0.423 | 0.804 | 0.998 | 0.341 | 0.423 | 0.804 | 0.998 |
| Sensitivity (%) | 75 | 91 | 88 | 75 | 90 | 96 | 100 | 100 |
| Specificity (%) | 89 | 90 | 90 | 90 | 75 | 77 | 86 | 82 |
| PPV (%) | 92 | 90 | 82 | 21 | 88 | 83 | 82 | 20 |
| NPV (%) | 69 | 92 | 93 | 99 | 80 | 94 | 100 | 100 |
| AUROC | 0.89 | 0.96 | 0.96 | 0.96 | 0.91 | 0.97 | 0.96 | 0.9 |

Ridge Regression Analysis:

$$\text{Disease Score} = -1.7588 + 0.1729 \times \log_2[uDN5](\text{ng/mg}) - 0.0971 \times \log_2[uDN2](\text{ng/mg}) + 0.2381 \times \log_2[uGR3](\text{ng/mg}) + 0.1312 \times \log_2[sDNO](\text{ng/ml})$$

TABLE 24

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 2.261 | 2.854 | 2.261 | 2.854 |
| Sensitivity (%) | 91 | 85 | 96 | 94 |
| Specificity (%) | 90 | 90 | 77 | 90 |

TABLE 24-continued

Cutoff Values Representing DN Early and Late Stages Indicated by Urine Albumin Levels

|  | Training set (n = 118) | | Testing set (n = 47) | |
|---|---|---|---|---|
|  | DM vs. DN | DM, Microalbuminuria vs. Macroalbuminuria | DM vs. DN | DM, Microalbuminuria vs. Macroalbuminuria |
| PPV (%) | 90 | 81 | 83 | 85 |
| NPV (%) | 92 | 92 | 94 | 96 |
| AUROC | 0.95 | 0.95 | 0.97 | 0.95 |

TABLE 25

Cutoff Values Representing DN Stages 1-5

|  | Training set (n = 118) | | | | Testing set (n = 47) | | | |
|---|---|---|---|---|---|---|---|---|
| DN-Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 2.079 | 2.261 | 2.854 | 3.950 | 2.079 | 2.261 | 2.854 | 3.950 |
| Sensitivity (%) | 77 | 91 | 85 | 75 | 87 | 96 | 94 | 100 |
| Specificity (%) | 89 | 90 | 90 | 90 | 69 | 77 | 90 | 82 |
| PPV (%) | 92 | 90 | 81 | 21 | 84 | 83 | 85 | 20 |
| NPV (%) | 70 | 92 | 92 | 99 | 73 | 94 | 96 | 100 |
| AUROC | 0.89 | 0.95 | 0.95 | 0.95 | 0.89 | 0.97 | 0.95 | 0.93 |

Five Protein Model

The combined levels of uDN2, uDN5, uGR3, uDNO, and sDNO in DM subjects and DN subjects were subjected to discriminant function analysis, logistic regression analysis, factor analysis, and ridge regression analysis. The results indicate that the combination of these five proteins or their fragments can be used as a reliable marker for determining DN stages.

Shown below are equations for calculating disease scores based on the combined levels of these five protein molecules, as well as tables (i.e., Tables 26-33) listing cutoff values, sensitivities, specificities, NPVs, PPVs, and AUROC for this five-protein model.

Discriminant Function Analysis:

$$\text{Disease Score} = 0.2780 \times \log_2[uDN5](ng/mg) + 0.0231 \times \log_2[uDN2](ng/mg) + 0.2236 \times \log_2[uGR3](ng/mg) + 0.6043 \times \log_2[sDNO](ng/ml) - 0.1513 \times \log_2[uDNO](ng/mg) + 5$$

TABLE 26

Cutoff Values Representing DN Early and Late Stages Indicated by Urine Albumin Levels

|  | Training set (n = 118) | | Testing set (n = 47) | |
|---|---|---|---|---|
|  | DM vs. DN | DM, Microalbuminuria vs. Macroalbuminuria | DM vs. DN | DM, Microalbuminuria vs. Macroalbuminuria |
| Cut-off | 11.818 | 12.164 | 11.818 | 12.164 |
| Sensitivity (%) | 86 | 98 | 96 | 100 |
| Specificity (%) | 90 | 90 | 86 | 86 |
| PPV (%) | 89 | 83 | 89 | 82 |
| NPV (%) | 87 | 99 | 95 | 100 |
| AUROC | 0.94 | 0.97 | 0.98 | 0.98 |

TABLE 27

Cutoff Values Representing DN States 1-5

|  | Training set (n = 118) | | | | Testing set (n = 47) | | | |
|---|---|---|---|---|---|---|---|---|
| DN Stages | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 11.766 | 11.818 | 12.164 | 14.432 | 11.766 | 11.818 | 12.164 | 14.432 |
| Sensitivity (%) | 73 | 86 | 98 | 100 | 81 | 96 | 100 | 100 |
| Specificity (%) | 89 | 90 | 90 | 90 | 88 | 86 | 86 | 82 |
| PPV (%) | 91 | 89 | 83 | 27 | 93 | 89 | 82 | 20 |
| NPV (%) | 67 | 87 | 99 | 100 | 70 | 95 | 100 | 100 |
| AUROC | 0.86 | 0.94 | 0.97 | 0.98 | 0.94 | 0.98 | 0.98 | 0.91 |

Factor Analysis:

Disease Score=$0.9117 \times \log_2[uDN5](\text{ng/mg}) + 0.6949 \times \log_2[uDN2](\text{ng/mg}) + 0.9095 \times \log_2[uGR3](\text{ng/mg}) + 0.4554 \times \log_2[sDNO](\text{ng/ml}) + 0.0384 \times \log_2[uDNO](\text{ng/mg})$

TABLE 28

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 29.475 | 30.541 | 29.475 | 30.541 |
| Sensitivity (%) | 81 | 93 | 88 | 100 |
| Specificity (%) | 90 | 90 | 91 | 83 |
| PPV (%) | 88 | 83 | 92 | 78 |
| NPV (%) | 83 | 96 | 87 | 100 |
| AUROC | 0.93 | 0.96 | 0.99 | 0.98 |

TABLE 29

Cutoff Values Representing DN Stages 1-5

| | Training set (n = 118) | | | | Testing set (n = 47) | | | |
|---|---|---|---|---|---|---|---|---|
| DN Stages | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 28.740 | 29.475 | 30.541 | 39.042 | 28.740 | 29.475 | 30.541 | 39.042 |
| Sensitivity (%) | 67 | 81 | 93 | 75 | 81 | 88 | 100 | 50 |
| Specificity (%) | 89 | 90 | 90 | 90 | 94 | 91 | 83 | 84 |
| PPV (%) | 91 | 88 | 83 | 21 | 96 | 92 | 78 | 12 |
| NPV (%) | 62 | 83 | 96 | 99 | 71 | 87 | 100 | 97 |
| AUROC | 0.84 | 0.93 | 0.96 | 0.95 | 0.92 | 0.99 | 0.98 | 0.86 |

Logistic Regression Analysis:

Disease Score=$\exp(\text{Logit\_value})/(1+\exp(\text{Logit\_value}))$, in which Logit_value=$-11.4318 + 0.8188 \times \log_2[uDN5](\text{ng/mg}) - 0.5376 \times \log_2[uDN2](\text{ng/mg}) + 0.7561 \times \log_2[uGR3](\text{ng/mg}) + 0.3940 \times \log_2[sDNO](\text{ng/ml}) - 0.1741 \times \log_2[uDNO](\text{ng/mg})$

TABLE 30

Cutoff Values Representing DN Early and Late Stages Indicated by Urine Albumin Levels

| | Training set (n = 118) | | Testing set (n = 47) | |
|---|---|---|---|---|
| | DM vs. DN | DM, Micro albuminuria vs. Macro albuminuria | DM vs. DN | DM, Micro albuminuria vs. Macro albuminuria |
| Cut-off | 0.436 | 0.780 | 0.436 | 0.780 |
| Sensitivity (%) | 91 | 93 | 96 | 100 |
| Specificity (%) | 90 | 90 | 77 | 86 |
| PPV (%) | 90 | 83 | 83 | 82 |
| NPV (%) | 92 | 96 | 94 | 100 |
| AUROC | 0.96 | 0.96 | 0.97 | 0.96 |

TABLE 31

Cutoff Values Representing DN States 1-5

| DN Stages | Training set (n = 118) | | | | Testing set (n = 47) | | | |
|---|---|---|---|---|---|---|---|---|
| | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 0.329 | 0.436 | 0.780 | 0.997 | 0.329 | 0.436 | 0.780 | 0.997 |
| Sensitivity (%) | 75 | 91 | 93 | 100 | 90 | 96 | 100 | 100 |
| Specificity (%) | 89 | 90 | 90 | 90 | 75 | 77 | 86 | 80 |
| PPV (%) | 92 | 90 | 83 | 27 | 88 | 83 | 82 | 18 |
| NPV (%) | 69 | 92 | 96 | 100 | 80 | 94 | 100 | 100 |
| AUROC | 0.89 | 0.96 | 0.96 | 0.96 | 0.91 | 0.97 | 0.96 | 0.91 |

Ridge Regression Analysis:

$$\text{Disease Score} = -1.3112 + 0.1648 \times \log_2[uDN5](\text{ng/mg}) - 0.0968 \times \log_2[uDN2](\text{ng/mg}) + 0.2468 \times \log_2[uGR3](\text{ng/mg}) + 0.1426 \times \log_2[sDNO](\text{ng/ml}) - 0.0552 \times \log_2[uDNO](\text{ng/mg})$$

TABLE 32

Cutoff Values Representing DN Early and Late Stages Indicated by Urine Albumin Levels

| | Training set (n = 118) | | Testing set (n = 47) | |
|---|---|---|---|---|
| | DM vs. DN | DM, Microalbuminuria vs. Macroalbuminuria | DM vs. DN | DM, Microalbuminuria vs. Macroalbuminuria |
| Cut-off | 2.244 | 2.729 | 2.244 | 2.729 |
| Sensitivity (%) | 91 | 88 | 96 | 100 |
| Specificity (%) | 90 | 90 | 82 | 90 |
| PPV (%) | 90 | 82 | 86 | 86 |
| NPV (%) | 92 | 93 | 95 | 100 |
| AUROC | 0.95 | 0.95 | 0.98 | 0.97 |

TABLE 33

Cutoff Values Representing DN Stages 1-5

| DN Stages | Training set (n = 118) | | | | Testing set (n = 47) | | | |
|---|---|---|---|---|---|---|---|---|
| | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 2.043 | 2.244 | 2.729 | 3.913 | 2.043 | 2.244 | 2.729 | 3.913 |
| Sensitivity (%) | 77 | 91 | 88 | 100 | 87 | 96 | 100 | 100 |
| Specificity (%) | 89 | 90 | 90 | 90 | 69 | 82 | 90 | 80 |
| PPV (%) | 92 | 90 | 82 | 27 | 84 | 86 | 86 | 18 |
| NPV (%) | 70 | 92 | 93 | 100 | 73 | 95 | 100 | 100 |
| AUROC | 0.89 | 0.95 | 0.95 | 0.96 | 0.9 | 0.98 | 0.97 | 0.93 |

EXAMPLE 3

Staging DN Based on a Combination of uDN2, uDN5, uGR3, and Age

Shown below are equations for calculating disease scores determined by discriminant function analysis, factor analysis, logistic regression analysis, and ridge regression analysis, based on the level of a biomarker composed of three protein molecules, i.e., uDN2, uDN5, and uGR3, and one clinical factor, i.e., age. Also shown below are tables (i.e., Tables 34-41) listing cutoff values, sensitivities, specificities, PPVs, NPVs, and AUROC for this model.

Discriminant Function Analysis:

$$\text{Disease Score} = 0.3342 \times \log_2[uDN5](\text{ng/mg}) - 0.0201 \times \log_2[uDN2](\text{ng/mg}) + 0.2826 \times \log_2[uGR3](\text{ng/mg}) + 0.0059 \times \text{Age}(\text{year}) + 5$$

TABLE 34

Cutoff Values Representing DN Early and Late Stages Indicated by Urine Albumin Levels

|  | Training set (n = 118) | | Testing set (n = 47) | |
| --- | --- | --- | --- | --- |
|  | DM vs. DN | DM, Micro albuminuria vs. Macro albuminuria | DM vs. DN | DM, Micro albuminuria vs. Macro albuminuria |
| Cut-off | 11.515 | 12.088 | 11.515 | 12.088 |
| Sensitivity (%) | 93 | 93 | 100 | 100 |
| Specificity (%) | 90 | 90 | 77 | 79 |
| PPV (%) | 90 | 83 | 83 | 75 |
| NPV (%) | 93 | 96 | 100 | 100 |
| AUROC | 0.95 | 0.96 | 0.98 | 0.97 |

TABLE 35

Cutoff Values Representing DN Stages 1-5

|  | Training set (n = 118) | | | | Testing set (n = 47) | | | |
| --- | --- | --- | --- | --- | --- | --- | --- | --- |
| DN-Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 11.353 | 11.515 | 12.088 | 14.343 | 11.353 | 11.515 | 12.088 | 14.343 |
| Sensitivity (%) | 75 | 93 | 93 | 75 | 84 | 100 | 100 | 100 |
| Specificity (%) | 89 | 90 | 90 | 90 | 75 | 77 | 79 | 80 |
| PPV (%) | 92 | 90 | 83 | 21 | 87 | 83 | 75 | 18 |
| NPV (%) | 69 | 93 | 96 | 99 | 71 | 100 | 100 | 100 |
| AUROC | 0.87 | 0.95 | 0.96 | 0.95 | 0.9 | 0.98 | 0.97 | 0.9 |

TABLE 36

Cutoff Values Representing DN Early and Late Stages Indicated by Urine Albumin Levels

|  | Training set (n = 118) | | Testing set (n = 47) | |
| --- | --- | --- | --- | --- |
|  | DM vs. DN | DM, Micro albuminuria vs. Macro albuminuria | DM vs. DN | DM, Micro albuminuria vs. Macro albuminuria |
| Cut-off | 38.341 | 40.075 | 38.341 | 40.075 |
| Sensitivity (%) | 82 | 85 | 96 | 100 |
| Specificity (%) | 90 | 90 | 86 | 83 |
| PPV (%) | 89 | 81 | 89 | 78 |
| NPV (%) | 85 | 92 | 95 | 100 |
| AUROC | 0.93 | 0.94 | 0.99 | 0.98 |

Factor Analysis:

$$\text{Disease Score} = 0.9184 \times \log_2[uDN5](\text{ng/mg}) + 0.7006 \times \log_2[uDN2](\text{ng/mg}) + 0.9005 \times \log_2[uGR3](\text{ng/mg}) + 0.1863 \times \text{Age(year)}$$

TABLE 37

Cutoff Values Representing DN Stages 1-5

|  | Training set (n = 118) | | | | Testing set (n = 47) | | | |
| --- | --- | --- | --- | --- | --- | --- | --- | --- |
| DN-Stages | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Number of patients (%) | 73 (62) | 57 (48) | 41 (35) | 4 (3) | 31 (66) | 25 (53) | 18 (38) | 2 (4) |
| Cut-off | 38.341 | 38.341 | 40.075 | 48.538 | 38.341 | 38.341 | 40.075 | 48.538 |
| Sensitivity (%) | 66 | 82 | 85 | 50 | 81 | 96 | 100 | 50 |
| Specificity (%) | 89 | 90 | 90 | 90 | 88 | 86 | 83 | 89 |
| PPV (%) | 91 | 89 | 81 | 15 | 93 | 89 | 78 | 17 |
| NPV (%) | 62 | 85 | 92 | 98 | 70 | 95 | 100 | 98 |
| AUROC | 0.82 | 0.93 | 0.94 | 0.91 | 0.9 | 0.99 | 0.98 | 0.77 |

Logistic Regression Analysis:

$$\text{Disease Score} = \exp(\text{Logit\_value})/(1 + \exp(\text{Logit\_value})), \text{ in which}$$

$$\text{Logit\_value} = -15.9748 + 0.8688 \times \log_2[uDN5](\text{ng/mg}) - 0.4966 \log_2[uDN2](\text{ng/mg}) + 0.6436 \times \log_2[uGR3](\text{ng/mg}) + 0.0879 \times \text{Age(year)}$$

TABLE 38

Cutoff Values Representing DN Early and Late Stages Indicated by Urine Albumin Levels

|  | Training set (n = 118) | | Testing set (n = 47) | |
|---|---|---|---|---|
|  | DM vs. DN | DM, Micro albuminuria vs. Macro albuminuria | DM vs. DN | DM, Micro albuminuria vs. Macro albuminuria |
| Cut-off | 0.321 | 0.889 | 0.321 | 0.889 |
| Sensitivity (%) | 93 | 80 | 100 | 94 |
| Specificity (%) | 90 | 90 | 77 | 83 |
| PPV (%) | 90 | 80 | 83 | 77 |
| NPV (%) | 93 | 90 | 100 | 96 |
| AUROC | 0.96 | 0.95 | 0.97 | 0.95 |

TABLE 39

Cutoff Values Representing DN Stages 1-5

|  | Training set (n = 118) | | | | Testing set (n = 47) | | | |
|---|---|---|---|---|---|---|---|---|
| DN-Stages | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 0.301 | 0.321 | 0.889 | 0.997 | 0.301 | 0.321 | 0.889 | 0.997 |
| Sensitivity (%) | 75 | 93 | 80 | 75 | 87 | 100 | 94 | 100 |
| Specificity (%) | 89 | 90 | 90 | 90 | 75 | 77 | 83 | 89 |
| PPV (%) | 92 | 90 | 80 | 21 | 87 | 83 | 77 | 29 |
| NPV (%) | 69 | 93 | 90 | 99 | 75 | 100 | 96 | 100 |
| AUROC | 0.89 | 0.96 | 0.95 | 0.92 | 0.88 | 0.97 | 0.95 | 0.91 |

Ridge Regression Analysis:

Disease Score=−2.1690+0.1771×$\log_2$[$uDN5$](ng/mg)−0.1074×$\log_2$[$uDN2$](ng/mg)+0.2474×$\log_2$[$uGR3$](ng/mg)+0.0168×Age(year)

TABLE 40

Cutoff Values Representing DN Early and Late Stages Indicated by Urine Albumin Levels

|  | Training set (n = 118) | | Testing set (n = 47) | |
|---|---|---|---|---|
|  | DM vs. DN | DM, Micro albuminuria vs. Macro albuminuria | DM vs. DN | DM, Micro albuminuria vs. Macro albuminuria |
| Cut-off | 2.139 | 2.880 | 2.139 | 2.880 |
| Sensitivity (%) | 93 | 85 | 100 | 89 |
| Specificity (%) | 90 | 90 | 73 | 83 |
| PPV (%) | 90 | 81 | 81 | 76 |
| NPV (%) | 93 | 92 | 100 | 92 |
| AUROC | 0.96 | 0.95 | 0.98 | 0.96 |

TABLE 41

Cutoff Values Representing DN Stages 1-5

|  | Training set (n = 118) | | | | Testing set (n = 47) | | | |
|---|---|---|---|---|---|---|---|---|
| DN-Stage | 1 vs. 2-5 | 1-2 vs. 3-5 | 1-3 vs. 4-5 | 1-4 vs. 5 | 1 vs. 2-5 | 1-2 vs. 3-5 | 1-3 vs. 4-5 | 1-4 vs. 5 |
| Cut-off | 2.128 | 2.139 | 2.880 | 4.051 | 2.128 | 2.139 | 2.880 | 4.051 |
| Sensitivity (%) | 75 | 93 | 85 | 75 | 84 | 100 | 89 | 100 |
| Specificity (%) | 89 | 90 | 90 | 90 | 69 | 73 | 83 | 89 |
| PPV (%) | 92 | 90 | 81 | 21 | 84 | 81 | 76 | 29 |
| NPV (%) | 69 | 93 | 92 | 99 | 69 | 100 | 92 | 100 |
| AUROC | 0.89 | 0.96 | 0.95 | 0.92 | 0.89 | 0.98 | 0.96 | 0.92 |

EXAMPLE 4

Initial identification of DN biomarkers

Midstream urinary specimens in the early morning were obtained from 22 healthy subjects without diabetic mellitus and with normal renal function, 44 patients with type 2 diabetic mellitus (DM), 48 patients with diabetic nephropathy (DN), and 20 patients with DN-caused-uremia. These urine samples were treated and analyzed by MALDI-TOF-MS.

Figure 2:
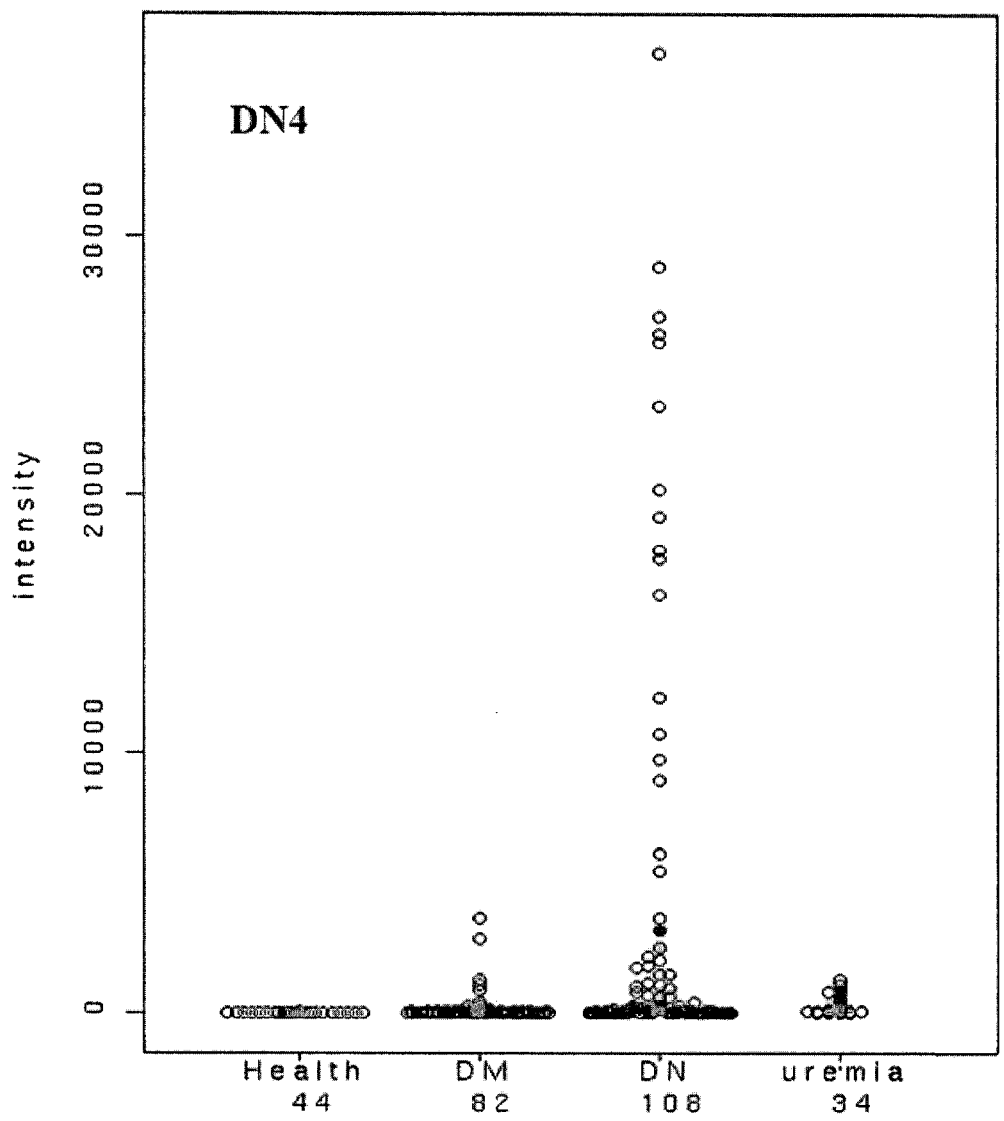
FIG. 2 is a graph showing MALDI-TOF-MS peak intensities from urine samples of control subjects and diabetic nephropathy (DN) patients. There was a significant increase in the peak intensity of Peak 4 (representing a unique peptide) in urine samples of DN patients as compared to healthy subjects, patients with diabetic mellitus without nephropathy (DM), and patients with diabetes and uremia.

Six significant peptides highly associated with DN were identified individually (for example, Peak 4 corresponding to a peptide is shown in FIG. 2). These peptides were identified as fragments of proteins DN2 and DN5. See Table 3 above.

Clinical samples were also collected from 5 healthy individuals, 5 DM patients with normal renal function, and 5 individuals with Dn manifesting microalbuminuria. Samples were examined with iTRAQ and separated by LC-MS/MS. Proteins with levels that significantly differed from the group were selected and further analyzed. Two additional Dn candidate biomarkers, i.e., DNO and annexin A2 (DNA), were identified.

Figure 3:
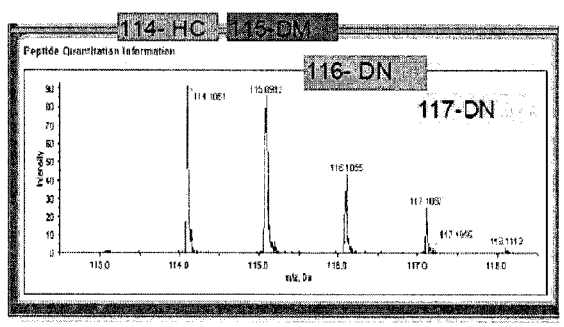
FIG. 3 includes a table and a graph showing that the level of an osteopontin (DNO) peptide in DN patients was decreased using isobaric tags for relative and absolute quantification (iTRAQ).

Decreases of urinary DNO level and urinary DNA level were apparent in individuals with DN. An increase of serum DNO can also be used to diagnose DN. Unique peptides from each of these two protein biomarkers were also identified to be of diagnostic value for DN. See, e.g., FIG. 3. The sequence of a DNO fragment, i.e., SEQ ID NO:8, is shown in Table 3 above.

Figure 4:
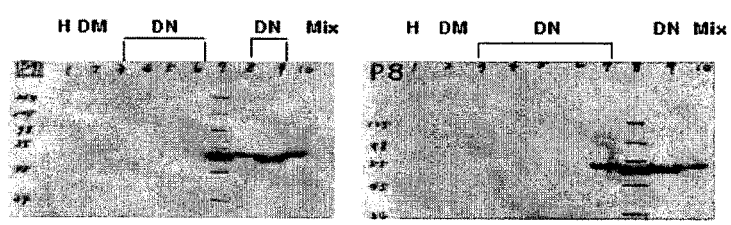
FIG. 4 is a set of Western blots obtained using antibodies generated against DN peptide biomarkers. H: healthy subject; DN: diabetic nephropathy patients; DM: diabetic patients without nephropathy.
Figure 4:
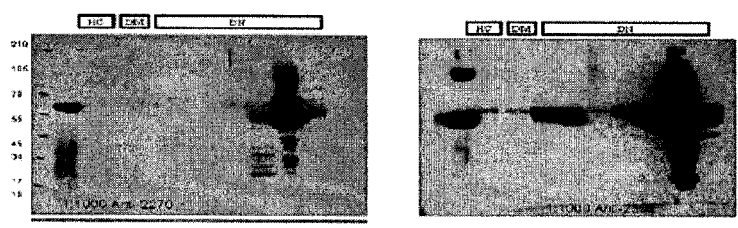
Figure 4:
Figure 4:
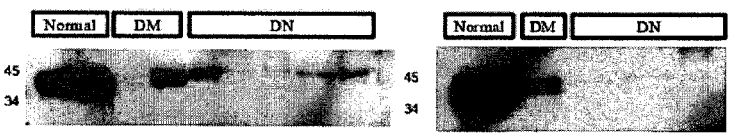

Polyclonal and monoclonal antibodies were generated against the above-described peptides. Urinary samples were collected from individuals with varying degrees of renal impairment identified by standard clinical parameters including albuminuria, serum creatinine level, and GFR. Urinary values were normalized by urine creatinine concentration. Western blot analysis was carried out using peptide-based antibodies. Significant decreases of urinary DNO level and DNA level, and significant increases of urinary DN2level, urinary DN5 level, and serum DNO level were noted in samples from DN patients as compared to healthy and DM controls. See FIG. 4.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of diagnosing diabetic nephropathy in a subject, comprising:
   obtaining a urine sample from a subject suspected of having diabetic nephropathy;
   determining the level of a biomarker in the urine sample, wherein the biomarker is a fragment of alpha-1 antitrypsin selected from the group consisting of (i) KGKWERPFEVKDTEEEDF (SEQ ID NO:3), (ii) MIEQNTKSPLFMGKVVNPTQK (SEQ ID NO:4), (iii) EDPQGDAAQKTDTSHHDQDHPTFNKITPNLAE (SEQ ID NO:5), and (iv) EDPQGDAAQKTDTSHHDQDHPTFNKITPNLAEFA (SEQ ID NO:6); and
   assessing whether the subject has diabetic nephropathy based on the level of the biomarker, wherein a higher level of the biomarker, as compared to that in a diabetic nephropathy-free subject, indicates that the subject has diabetic nephropathy, the level of the biomarker being determined with an antibody that specifically binds to the biomarker.

2. The method of claim 1, wherein the fragment of alpha-1 antitrypsin is KGKWERPFEVKDTEEEDF (SEQ ID NO:3).

3. The method of claim 1, wherein the fragment of alpha-1 antitrypsin is MIEQNTKSPLFMGKVVNPTQK (SEQ ID NO:4).

4. The method of claim 1, wherein the fragment of alpha-1 antitrypsin is EDPQGDAAQKTDTSHHDQDHPTFNKITPNLAE (SEQ ID NO:5).

5. The method of claim 1, wherein the fragment of alpha-1 antitrypsin is EDPQGDAAQKTDTSHHDQDHPTFNKITPNLAEFA (SEQ ID NO:6).

6. The method of claim 1, further comprising, after the assessing step, correlating the level of the biomarker with diabetic nephropathy status based on pre-determined reference levels of the biomarker representing early and late stage diabetic nephropathy.

7. A method for determining diabetic nephropathy stage in a subject, comprising:
   obtaining a urine sample, and optionally, a serum sample, from a subject suspected of having diabetic nephropathy;
   determining the level of each of a plurality of biomarkers in the sample(s), and optionally, one or more clinical factors, the one or more clinical factors being selected from the group consisting of age, gender, HbA1c, albumin/creatinine ratio, and glomerular filtration rate, wherein the plurality of biomarkers include:
   (a) a first urine biomarker that is a fragment of alpha-1 antitrypsin selected from the group consisting of (i) KGKWERPFEVKDTEEEDF (SEQ ID NO:3), (ii) MIEQNTKSPLFMGKVVNPTQK (SEQ ID NO:4), (iii) EDPQGDAAQKTDTSHHDQDHPTFNKITPNLAE (SEQ ID NO:5), and (iv) EDPQGDAAQKTDTSHHDQDHPTFNKITPNLAEFA (SEQ ID NO:6); and
   (b) one or more biomarkers selected from the group consisting of (i) a second urine biomarker that is precursor alpha-2-HS-glycoprotein, VVSLGSPSGEVSHPRKT (SEQ ID NO:1), or MGVVSLGSPSGEVSHPRKT (SEQ ID NO:2), (ii) a third urine biomarker that is alpha-1 acid glycoprotein or GQEHFAHLLILRDTKTYMLAFDVNDEKNWGLS (SEQ ID NO:7), (iii) a fourth urine biomarker that is osteopontin or YPDAVATWLNPDPSQKQNLLAPQNAVSSEETNDFKQETLPSK (SEQ ID NO:8), and (iv) if the optional serum sample is obtained, a serum biomarker that is osteopontin or YPDAVATWLNPDPSQKQNLLAPQNAVSSEETNDFKQETLPSK (SEQ ID NO:8);
   calculating a disease score based on the levels of the plurality of biomarkers, and optionally, the one or more clinical factors; and
   assessing the diabetic nephropathy stage of the subject based on the disease score as compared to pre-determined cutoff values that indicate different diabetic nephropathy stages, wherein the levels of the plurality of biomarkers are determined with antibodies that specifically bind to the biomarkers.

8. The method of claim 7, wherein the disease score is calculated by an analysis selected from the group consisting of ridge regression analysis, factor analysis, discriminant function analysis, and logistic regression analysis.

9. The method of claim 7, wherein the plurality of biomarkers include the third urine biomarker.

10. The method of claim 7, wherein the plurality of biomarkers include the second urine biomarker and the third urine biomarker.

11. The method of claim 7, wherein the plurality of biomarkers include the second urine biomarker, the third urine biomarker, and the serum biomarker.

12. The method of claim 7, wherein the plurality of biomarkers include the second urine biomarker, the third urine biomarker, the fourth urine biomarker, and the serum biomarker.

13. The method of claim 7, wherein the disease score is calculated based on one or more clinical factors.

14. The method of claim 7, wherein the fragment of alpha-1 antitrypsin is KGKWERPFEVKDTEEEDF.

15. A method for monitoring diabetic nephropathy progress in a subject, comprising:

obtaining a first urine sample, and optionally, a first serum sample, from a subject suspected of having diabetic nephropathy;

obtaining a second urine sample, and optionally, a second serum sample, 2 weeks to 12 months later;

determining the level of each of a plurality of biomarkers in the first and second samples, and optionally, one or more clinical factors, the one or more clinical factors being selected from the group consisting of age, gender, HbA1c, albumin/creatinine ratio, and glomerular filtration rate, wherein the plurality of biomarkers include:

(a) a first urine biomarker that is a fragment of alpha-1 antitrypsin selected from the group consisting of (i) KGKWERPFEVKDTEEEDF (SEQ ID NO:3), (ii) MIEQNTKSPLFMGKVVNPTQK (SEQ ID NO:4), (iii) EDPQGDAAQKTDTSHHDQDHPTFNKITPNLAE (SEQ ID NO:5), and (iv) EDPQGDAAQKTDTSHHDQDHPTFNKITPNLAEFA (SEQ ID NO:6); and (b) one or more biomarkers selected from the group consisting of (i) a second urine biomarker that is precursor alpha-2-HS-glycoprotein, VVSLGSPSGEVSHPRKT (SEQ ID NO:1), or MGVVSLGSPSGEVSHPRKT (SEQ ID NO:2), (ii) a third urine biomarker that is alpha-1 acid glycoprotein or GQEHFAHLLILRDTKTYMLAFDVNDEKNWGLS (SEQ ID NO:7), (iii) a fourth urine biomarker that is osteopontin or YPDAVATWLNPDPSQKQNLLAPQNAVSSEETNDFKQETLPSK (SEQ ID NO:8), and (iv) if the optional first and second serum samples are obtained, a serum biomarker that is osteopontin or YPDAVATWLNPDPSQKQNLLAPQNAVSSETNDFKQETLPSK (SEQ ID NO:8);

calculating a first disease score and a second disease score based on the levels of the plurality of biomarkers in the first and second samples, respectively, and optionally, on the one or more clinical factors; and assessing disease progress in the subject, wherein the second disease score being greater than the first disease score is indicative of diabetic nephropathy exacerbation, wherein the levels of the plurality of biomarkers are determined with antibodies that specifically bind to the biomarkers.

16. The method of claim 15, wherein the disease score is calculated by an analysis selected from the group consisting of ridge regression analysis, factor analysis, discriminant function analysis, and logistic regression analysis.

17. The method of claim 15, wherein the plurality of biomarkers include the third urine biomarker.

18. The method of claim 15, wherein the plurality of biomarkers include the second urine biomarker and the third urine biomarker.

19. The method of claim 15, wherein the plurality of biomarkers include the second urine biomarker, the third urine biomarker, and the serum biomarker.

20. The method of claim 15, wherein the plurality of biomarkers include the second urine biomarker, the third urine biomarker, the fourth urine biomarker, and the serum biomarker.

21. The method of claim 15, wherein the disease score is calculated based on one or more clinical factors.

22. The method of claim 15, wherein the fragment of alpha-1 antitrypsin is KGKWERPFEVKDTEEEDF.

* * * * *